United States Patent
Kalchauer et al.

(10) Patent No.: US 7,368,590 B2
(45) Date of Patent: May 6, 2008

(54) METHOD FOR SEPARATING ALUMINIUM CHLORIDE FROM ORGANOCHLOROSILANES

(75) Inventors: Wilfried Kalchauer, Burghausen (DE); Herbert Straussberger, Mehring (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 10/598,850

(22) PCT Filed: Mar. 17, 2005

(86) PCT No.: PCT/EP2005/002886

§ 371 (c)(1),
(2), (4) Date: Sep. 13, 2006

(87) PCT Pub. No.: WO2005/092903

PCT Pub. Date: Oct. 6, 2005

(65) Prior Publication Data

US 2007/0193696 A1 Aug. 23, 2007

(30) Foreign Application Priority Data

Mar. 23, 2004 (DE) .................. 10 2004 014 220

(51) Int. Cl.
C07F 7/04 (2006.01)
C01F 7/62 (2006.01)

(52) U.S. Cl. .................... 556/484; 423/496
(58) Field of Classification Search .................... None
See application file for complete search history.

(56) References Cited

U.S. PATENT DOCUMENTS

| 2,557,782 A | | 6/1951 | Clark et al. |
| 5,434,286 A | * | 7/1995 | Geisberger .................. 556/469 |
| 6,077,967 A | | 6/2000 | Cardinaud et al. |

FOREIGN PATENT DOCUMENTS

| DE | 842057 | 6/1952 |
| DE | 1111183 | 2/1962 |
| EP | 0 155 626 | 9/1985 |
| EP | 0 829 484 A2 | 3/1998 |
| FR | 2 761 360 A1 | 10/1998 |
| JP | 20005-029428 | * 3/2005 |

OTHER PUBLICATIONS

Stark et al., "Aluminum Compounds, Inorganic," Ullmann's Encyclopedia of Industrial Chemistry, 2002, Wiley-VCH Verlag.
Nol, W., Chemistry and Technology of Silicones, 1968, pp. 238 and 340-342.
Lewis et al., "Catalyzed Direct Reactions of Silicon," Studies in Organic Chemistry 49, 1993, Chapter 1, p. 18.
Roesch et al., "Silicon Compounds, Organic," Ullmann's Encyclopedia of Industrial Chemistry, vol. A 24, p. 26.
Schmoelzer H., et al., "Äquilibrierungsreaktionen an Disilanen," Journal of Organometallic Chemistry, vol. 260, No. 1, Jan. 3, 1984, pp. 31-39 (and English translation).
Sakurai et al., "Aluminum Chloride-Catalyzed Reactions of Organosilicon Compounds II. Facile Syntheses of Alkylchlorosilanes, -Germanes, and -Stannanes (1)," Tetrahedron Letters, vol. 7, No. 45, 1966, pp. 5493-5497.
Zemany, et al., "Kinetics and Thermodynamic Properties of the Disproportionation of Methylchlorosilanes," Journal of the American Chemical Society, vol. 70, No. 12, (1948-12), pp. 4222-4226.
Sauer et al., "Thermal Transformations of Methylchlorosilanes," Journal of the American Chemical Society, vol. 70, No. 11, (1948-11), pp. 3590-3596.
For FR 2 761 360: English Patbase Abstract.
For EP-A 155626: English Patbase Abstract.
For DE-B 1111183: English Patbase Abstract.
For DE-C 842057: English Patbase Abstract.

* cited by examiner

*Primary Examiner*—Paul A. Zucker
(74) *Attorney, Agent, or Firm*—Brooks Kushman P.C.

(57) ABSTRACT

Aluminum chloride is removed effectively from compound mixtures containing organochlorosilanes such as are produced in the direct synthesis, by adding a diluent containing organochlorosilanes and optionally chloromethane to a solids content <15% and a concentration of compounds having a boiling point >71° C. of less than 25%, and evaporating this diluted mixture into a volatile product stream and an $AlCl_3$-containing solid.

7 Claims, No Drawings

METHOD FOR SEPARATING ALUMINIUM CHLORIDE FROM ORGANOCHLOROSILANES

CROSS-REFERENCE TO RELATED APPLICATION

This application is the U.S. national phase of PCT Appln. No. PCT/EP2005/002886 filed Mar. 17, 2005, which claims priority to German application 10 2004 014 220.3 filed Mar. 23, 2004.

BACKGROUND OF THE INVENTION

1. Field of the Invention

The invention relates to a process for removing $AlCl_3$ from organochlorosilane mixtures.

2. Description of the Related Art

In the preparation of organochlorosilanes, product streams are obtained which may comprise aluminium chloride in different concentrations as a function of the process/operation. Depending on the conditions, for example the temperature and the chemistry of the organosilanes, the $AlCl_3$ is dissolved at least partly in the liquid organochlorosilane stream and thus cannot be removed by filtration. Being a Lewis acid, $AlCl_3$ can exert highly disruptive influences depending on the process temperature.

An effective distillative removal of organochlorosilanes and $AlCl_3$ is possible only at moderate temperatures up to about 150° C., since $AlCl_3$ exhibits the tendency to sublime and at least partly distils overhead with the organochlorosilanes when higher temperatures are employed. According to Ullmann's Encyclopaedia of Industrial Chemistry, $AlCl_3$ has a sublimation temperature of 181.2° C. at 101.3 kPa.

According to Ullmann's Encyclopaedia of Industrial Chemistry, $AlCl_3$ has a sublimation temperature of 181.2° C. at 101.3 kPa.

Disruptive Influences of $AlCl_3$ are, for example:

1. At relatively high temperatures, $AlCl_3$ reacts with siloxanes, for example methylchlorodisiloxanes, to form aluminosiloxanes. Depending on the degree of branching of these aluminosiloxanes, they are viscous to solid and can thus clog process equipment such as pipelines, or greatly reduce heat transfer as a result of deposits in the region of heated process equipment such as heat exchangers. The formation of such aluminosiloxanes is described, for example, in "W. Noll, Chemistry and Technology of Silicones, 1968, pages 238 and 340-342 (1).

2. $AlCl_3$, even at low temperatures, is an excellent catalyst for the exchange of the organic ligands and the Cl and H ligands in organochlorosilanes, especially in the presence of Si—H compounds. These reactions are sometimes used selectively for the preparation of certain organochlorosilanes. However, this ligand exchange may also be disruptive when the $AlCl_3$ has not been added deliberately and the product spectrum is thus shifted in an undesired direction. Such ligand exchange reactions are described, for example, in (1), pages 57-66 and J. Organomet. Chem. 260 (1984), 31-39, H. Schmölzer, E. Hengge (2).

FR 2761360 states that, for example, the selective addition of compounds of the (R)—Si—(OR) type can reduce the catalytic effectiveness of $AlCl_3$ in relation to ligand exchange. However, this method has the following disadvantages: an additional substance has to be used, which increases cost, and subsequently has to be destroyed/disposed of again, and which complicates the distillative workup of the organochlorosilanes.

3. $AlCl_3$ catalyses the decomposition of methylchlorodisilanes in the direction of methylchloromonosilanes and oligo-/polysilanes; in the presence of Si—H bonds, this reaction begins at as low as from approx. 105° C. The oligo-/polysilanes formed may be viscous to solid and insoluble, and may induce the problems described under point 1. The formation of these oligo-/polysilanes is described, for example, in (2).

The presence of $AlCl_3$ is particularly disruptive in the processes below:

1. Direct Synthesis of Methylchlorosilanes According to Müller-Rochow.

In the direct synthesis of methylchlorosilanes, silicon is reacted with MeCl in the presence of various catalysts at about 265-310° C. This forms a mixture of various methylchloro(hydro)silanes, and also methylchlorodisilanes, methylchlorodisiloxanes and hydrocarbons. The Si used typically contains 0.1-0.3% Al, and an increase in the amount of Al, for example by adding an aluminum-containing alloy to the reaction system is likewise known. Irrespective of the source and of the form used, $AlCl_3$ forms at least partly from the aluminium and, owing to the temperatures, the system comprising the reaction products and unconverted starting materials leaves via the gas phase.

In "Catalysed Direct Reactions of Silicon; K.M. Lewis, D.G. Rethwisch; Elsevier 1993; Chapter 1" (3), FIG. 3 on page 18 shows a schematic flow diagram of the process, in which the solid-containing reaction products from the direct synthesis are condensed, the solids are removed and the crude silane is fed to the distillation. "Ullmann's Encyclopaedia of Industrial Chemistry Vol. A 24, page 26" describes a similar process.

The liquid crude silane mixture prepared in this way comprises, in addition to the methylchloromonosilanes, also $AlCl_3$, methylchlorodisilanes, disiloxanes and hydrocarbons. This means that the reactions described under "disruptive influences" occur during the distillative workup even when only the filtered crude silane mixture freed of solid is used further.

In (3) on page 22-28, the following further workup method is specified as an alternative:

"Gases separated in the cyclone and filter are fed into the bottom of a scrubber in which products with normal boiling points less than about 170° C. are separated from metal chlorides and other higher boilers. The distillate is fractionated into an overhead stream containing compounds boiling at or below 71° C. and a side stream composed essentially of the cleavable disilanes. The bottoms, containing solids and methylchlorosilanes, are purged periodically and sent to waste disposal."

The disadvantages in this process are: Since the methylchlorosilanes are a mixture of many different substances having a wide boiling point range, it is not possible simultaneously to drive all utilizable products out of the bottoms of the scrubber and/or of the fractionation unit and to keep the temperature for the driving-out of the organochlorosilanes so low that the disadvantages described do not occur. In other words, the scrubber or the fractionation unit is operated at temperatures at which the reactions catalysed by $AlCl_3$ do not occur to a noticeable extent, and the loss of utilizable methylchloro(di)silanes is automatically accepted. However, when these plants are operated at a higher temperature at which almost all utilizable products are driven out, the undesired side reactions occur to an increased extent, and the higher-boiling fractions, for example the disilane fraction, simultaneously comprise not inconsiderable proportions of entrained $AlCl_3$. The residues which occur are suspensions composed of liquid organochlorosilanes and solids. A workup or disposal of such product streams is generally to be classified as problematic.

When FIGS. 4 and 5, page 25, 26 and illustrative text in (3) are considered, it can be seen that the $AlCl_3$ introduced with the crude MCS direct reaction mixture is discharged with the disilanes in the direction of column A and will cause the problems already described many times, in this region or in the downstream disilane workup at the latest.

2. $AlCl_3$-catalysed High Boiler Workup.

EP 829484 A, for example, describes the $AlCl_3$-catalysed cleavage of high boilers from methylchlorosilane synthesis by means of HCl or H2 or corresponding mixtures. EP 155626 A, for example, describes the $AlCl_3$-catalysed conversion of high boilers and low boilers in the direction of more utilizable monosilanes. In the workup of these reaction products, comparable problems occur to those which have been described for the direct synthesis.

3. Amine-catalysed Disilane Cleavage.

Various methylchlorodisilanes which are obtained as a by-product in direct synthesis may be converted using hydrogen chloride directly to methylchloromonosilanes (disilane cleavage). This reaction is catalysed, for example, by tertiary amines such as tributylamine, and is described in (3) on page 30-31. However, $AlCl_3$ forms complexes with amines which have only a greatly reduced, if any, catalytic activity, i.e. when $AlCl_3$ is present in sufficient amounts in the disilane cleavage, the reaction comes to a standstill.

SUMMARY OF INVENTION

It is an object of the invention to provide a process which enables the $AlCl_3$ and any further solids to be removed from $AlCl_3$-containing organochlorosilane streams in a simple manner even when a conventional distillative separation is not effective owing to the boiling point of the organochlorosilanes.

The invention provides a process for removing $AlCl_3$ from a compound mixture (C1) comprising organochlorosilanes and having an $AlCl_3$ content of >200 ppm based on the content of organochlorosilanes, in which the compound mixture (C1) is diluted with compounds (C2) which are selected from organochlorosilanes or mixtures of chloromethane and organochlorosilanes in such a way that a product stream (P) with <15% solids at a simultaneous concentration of <25% of components having a boiling point >71° C. at 1013 hPa is obtained, and this product stream (P) is separated in an evaporator unit at a temperature <165° C. into volatile compounds (VC) and $AlCl_3$-containing solid (S), all concentration data being based on the weight.

DETAILED DESCRIPTION OF THE PREFERRED EMBODIMENTS

By virtue of the dilution of the compound mixture (C1) with the substantially solids- and high boiler-free compounds (C2), as a result of the "entrainment effect", even organochlorosilanes having a boiling point which is above the evaporator temperature are virtually fully evaporated, so that the $AlCl_3$-containing solid (S) obtained is dry and can thus be handled in a simple manner.

The compound mixture (C1) stems preferably from the workup of the product mixture from the direct synthesis of alkylchlorosilanes, or from the $AlCl_3$-catalysed high boiler cleavage of the by-products of the direct synthesis.

In the direct synthesis of alkylchlorosilanes of the general formula (I), $R_aH_bSiCl_{4-a-b}$, in which a is 1, 2, 3 or 4 and b is 0, 1 or 2, from silicon metal and alkyl chlorides R—Cl where R is an alkyl radical, the by-products formed are di- and oligosilanes, carbosilanes, siloxanes and high-boiling cracking products.

The compound mixture (C1) comprising organochlorosilanes has an $AlCl_3$ content of preferably >300 ppm, more preferably >500 ppm. In addition to $AlCl_3$, the compound mixture (C1) may comprise further substances in dissolved or undissolved form.

The concentration of organosilanes having a boiling point of about 71° C. in the compound mixture (C1) is preferably >25%, more preferably >35%, in particular >45%.

The compound mixture (C2) has an $AlCl_3$ content of preferably <50 ppm, more preferably <30 ppm, in particular <20 ppm. The concentration of organosilanes having a boiling point of above 71° C. in the compound mixture (C2) is preferably <5%, more preferably <3%, in particular <1%. The compound mixture (C2) may comprise further volatile components, for example chloromethane.

The mixing ratio of (C1) and (C2) is adjusted such that the solids content of the resulting product stream (P) is <15% by weight, preferably <8% by weight, more preferably <4% by weight, and the content of components having a boiling point above 71° C. is <25%, preferably <15%, more preferably <10%. If desired, it is possible to add, in addition to the compound mixtures (C1) and (C2), further solids-containing streams, for example silicon dusts from the direct synthesis which are no longer utilizable or suspensions of Si dusts from the direct synthesis, as are obtained, for example, in cyclones, filters and sludges, with the proviso that the abovementioned features for the product stream (P) are maintained. On this subject, FIG. 3 in (3) is incorporated by reference.

The product stream (P) is separated preferably at <155° C., more preferably at <145° C. The evaporator unit is configured in such a way that the separation is effected very rapidly into substantially dry solids (F) and gaseous volatile compounds (VC). Those skilled in the art also refer to such a separation as a flash evaporation, i.e. there is no still/bottom in which the product stream (P) is heated continuously. Such an evaporator unit may, for example, be a unit for spray evaporation, thin-layer or thin-film evaporation.

If desired, it is possible in the course of the rapid evaporation for further volatile or gaseous compounds to be metered in in such a way that the removal of the evaporated volatile compounds (VC) is favoured. However, these compounds have to behave in a chemically inert manner in the system. The gaseous components used may, for example, be noble gases or nitrogen; the volatile compounds used may, for example, be chloromethane.

The volatile compounds (VC) drawn off in gaseous form are substantially free of undesired $AlCl_3$ impurities; solids entrained in the evaporation may, if desired, once more be removed by means of filtration before or after the condensation.

All temperatures reported relate to atmospheric pressure (1013 hPa). The process according to the invention may also be employed at reduced and at elevated pressure. Since the sublimation temperatures and most of the boiling temperatures depend greatly on the pressure, the temperatures in these cases change correspondingly.

All concentration data reported are based on the weight.

EXAMPLES

Apparatus:

A three-necked glass flask with attached dropping funnel, gas inlet and heat-insulated gas outlet is immersed into an electrically heated oil bath with the temperature [T]. If required, nitrogen may be introduced into the system via the gas inlet; the product steam [P] is metered in at such a rate that no noticeable fractions of liquid products are present in the heated flask in the steady state. The evaporated organochlorosilanes, hydrocarbons, chlorohydrocarbons and any nitrogen fed in leave the flask via the insulated gas outlet and are fed to a condensation system cooled with dry ice [D=condensate]. The solids introduced with the product stream [P] and most of the metal chlorides dissolved in [P] remain substantially in the flask.

The organochlorosilanes, hydrocarbons, chlorohydrocarbons were analysed by means of GC. The aluminium contents in the organochlorosilanes were determined, and the solids were analysed, by means of ICP.

All examples were carried out at standard pressure.

Comparative Example 1

The intention was to prove that a conventional distillation cannot effectively remove high-boiling organochlorosilanes and $AlCl_3$.

In a typical laboratory batchwise distillation system, $AlCl_3$ and solid-containing crude silane mixture are subjected to a fractional distillation up to a bottom temperature of 167° C. The resulting solids-free distillates 1-A to 1-E and the solids-containing liquid residue 1-R were analysed. The results are listed in 5 Table 1.

TABLE 1

| Fraction | 1-A | 1-B | 1-C | 1-D | 1-E | 1-R |
| --- | --- | --- | --- | --- | --- | --- |
| Top temperature (° C.) | 20-65 | 65-70 | 70-75 | 75-78 | 78-160 | |
| Sum of dimethyltetra-chlorodisilane and tri-methyltrichlorodisilane | 3.5 | 3.7 | 8.2 | 12.3 | 78.8 | 83.7 |
| Compounds having a boiling point >75° C., without dimethyltetra-chlorodisilane and tri-methyltrichlorodisilane | 1.3 | 1.3 | 4.4 | 3.4 | 11.3 | 15.9 |
| Aluminium content (ppm) | <3 | <3 | 3 | 4 | 185 | 8200 |

Examples 2-4

The product streams [C1] and [C2] and 3% by weight of ultrafine silicon dusts, as described in (3), FIG. 3, "Filter" were mixed in such a ratio that the product stream [P] was formed. This mixture was metered into 15 the apparatus described at an oil bath temperature of 140° C., 150° C. and 160° C., and a gentle nitrogen stream was additionally fed in via the gas inlet. In all cases, the thus obtained solids-free condensates [D] contained an Al content of <2 ppm. The results are 20 listed in Table 2.

TABLE 2

| | C-1 | C-2 | P |
| --- | --- | --- | --- |
| Chloromethane | 0 | 5.9 | 4.9 |
| Dimethylchlorosilane | 0 | 0.7 | 0.5 |
| Methyldichlorosilane | 0 | 8.2 | 7.3 |
| Trimethylchlorosilane | 0.2 | 3.8 | 3.3 |
| Methyltrichlorosilane | 0.8 | 7.3 | 6.6 |
| Dimethyldichlorosilane | 41.9 | 72.0 | 70.1 |
| Sum of dimethyltetrachlorodisilane and trimethyltrichlorodisilane | 47.7 | 0.0 | 4.8 |
| Compounds having a boiling point >71° C., without dimethyltetrachlorodisilane and trimethyltrichlorodisilane | 9.4 | 2.1 | 2.6 |
| Aluminium content (ppm) | 750 | 5 | 80 |

Example 5

Analogous to Example 2-4, with the alteration that the mixing ratio of [C1] and [C2] was altered and the product stream [P] thus had the composition below; the oil bath temperature was 160° C. The thus obtained solids-free condensate [D] contained an Al content of 6 ppm. The results are listed in Table 3.

TABLE 3

| | P |
| --- | --- |
| Chloromethane | 4.4 |
| Dimethylchlorosilane | 0.5 |
| Methyldichlorosilane | 6.5 |
| Trimethylchlorosilane | 3.1 |
| Methyltrichlorosilane | 6.0 |
| Dimethyldichlorosilane | 66.2 |
| Sum of dimethyltetrachlorodisilane and trimethyltrichlorodisilane | 9.6 |
| Compounds having a boiling point >71° C., without dimethyltetrachlorodisilane and trimethyltrichlorodisilane | 3.6 |
| Aluminium content (ppm) | 170 |

Example 6

Analogous to Example 2-4, with the alteration that a different compound mixture [C2] was used, the additional metering of Si dusts was dispensed with and no nitrogen was metered into the system during the experiment. The thus obtained solids-free condensate [D] contained an Al content of <2 ppm. The results are listed in Table 4.

TABLE 4

|  | C-1 | C-2 | P |
|---|---|---|---|
| Dimethylchlorosilane | 0 | 0.2 | 0.2 |
| Methyldichlorosilane | 0 | 3.0 | 2.7 |
| Trimethylchlorosilane | 0.2 | 2.1 | 1.9 |
| Methyltrichlorosilane | 0.8 | 6.0 | 5.5 |
| Dimethyldichlorosilane | 41.9 | 87.8 | 83.2 |
| Sum of dimethyltetrachlorodisilane and trimethyltrichlorodisilane | 47.7 | 0.0 | 4.8 |
| Compounds having a boiling point >71° C., without dimethyltetrachlorodisilane and trimethyltrichlorodisilane | 9.4 | 1.0 | 1.8 |
| Aluminium content (ppm) | 750 | <5 | 70 |

The invention claimed is:

1. A process for removing $AlCl_3$ from a compound mixture comprising organochlorosilanes and having an $AlCl_3$ content of >200 ppm based on the weight of organochlorosilanes, comprising diluting the compound mixture with diluent comprising organochlorosilanes or mixtures of chloromethane and organochlorosilanes to form a product stream with <15 weight percent solids at a simultaneous concentration of <25 weight percent of components having a boiling point >71° C. at 1013 hPa, and separating this product stream in an evaporator unit at a temperature <165° C. into volatile compounds and $AlCl_3$-containing solid.

2. The process of claim 1, wherein the compound mixture is derived from the direct synthesis of alkylchlorosilanes, or from the $AlCl_3$-catalysed high boiler cleavage of by-products of the direct synthesis.

3. The process of claim 1, wherein the organochlorosilanes are alkylchlorosilanes of the formula $R_aH_bSiCl_{4-a-b}$ in which a is 1, 2, or 3, b is 0, 1 or 2, R is a methyl, ethyl, butyl or propyl radical, and at least one chlorine is present.

4. The process of claim 2, wherein the organochlorosilanes are alkylchlorosilanes of the formula $R_aH_bSiCl_{4-a-b}$ in which a is 1, 2, or 3, b is 0, 1 or 2, R is a methyl, ethyl, butyl or propyl radical, and at least one chlorine is present.

5. The process of claim 1, wherein the evaporator unit used is a spray evaporator, thin-layer evaporator, or thin-film evaporator.

6. The process of claim 2, wherein the evaporator unit used is a spray evaporator, thin-layer evaporator, or thin-film evaporator.

7. The process of claim 4, wherein the evaporator unit used is a spray evaporator, thin-layer evaporator, or thin-film evaporator.

* * * * *